(12) United States Patent
Vitkalova et al.

(10) Patent No.: US 7,981,409 B2
(45) Date of Patent: Jul. 19, 2011

(54) METHOD OF REDUCING AGING OF SKIN BY APPLYING INTERLEUKIN-1 ALPHA

(75) Inventors: Tamara Aleksandrovna Vitkalova, Moscow (RU); Igor Anatolievich Pomytkin, Moscow (RU); Igor Arturovich Petropavlov, Zurich (RU)

(73) Assignee: United Technologies UT AG, Schlieren (CH)

( * ) Notice: Subject to any disclaimer, the term of this patent is extended or adjusted under 35 U.S.C. 154(b) by 30 days.

(21) Appl. No.: 12/423,115

(22) Filed: Apr. 14, 2009

(65) Prior Publication Data

US 2009/0263350 A1    Oct. 22, 2009

Related U.S. Application Data

(63) Continuation-in-part of application No. PCT/EP2008/054574, filed on Apr. 16, 2008.

(51) Int. Cl.
*A61K 38/20* (2006.01)

(52) U.S. Cl. .................................. 424/85.2; 514/887

(58) Field of Classification Search .................. None
See application file for complete search history.

(56) References Cited

U.S. PATENT DOCUMENTS

| 5,534,251 | A | * | 7/1996 | Sugahara et al. | ............ 424/85.2 |
| 6,022,896 | A | | 2/2000 | Weinkauf et al. | |
| 6,919,072 | B2 | | 7/2005 | Varani et al. | |

FOREIGN PATENT DOCUMENTS

| EP | 0 391 444 A2 | 10/1990 |
| EP | 1 849 501 A2 | 10/2007 |
| WO | WO 2005/091891 A2 | 10/2005 |
| WO | WO 2006/097359 | * 9/2006 |
| WO | WO 2006/097359 A1 | 9/2006 |

OTHER PUBLICATIONS

Postlethwaite et al (1988), The Journal of Cell Biology, vol. 106, pp. 311-318.*
Duncan et al (1989), The Society for Investigative Dermatology, vol. 92, pp. 699-706.*
"Photoaging: Mechanisms and repair", (Jessica H. Rabe, MD, et al.) Continuing Medical Education (Baltimore, Maryland) Jul. 2006.
"The interlukin-1 family: 10 years of Discovery", (Charles A. Dinarello) The FASEB Journal, vol. 8 (Dec. 1994).
"Chemical Peels", (Marina Landau, MD) Clinics in Dermatology Sep. 2007.
International Search Report and Written Opinion in PCT/EP2008/054574.
Mauviel et al., Comparative effects of interleukin-1 and tumor necrosis factor-alpha . . . , J Invest Dermatol. Feb. 1991;96(2):243-9.
Masamitsu et al., Photoaging of the skin. Anti-aging Medicine 6(6): 46-59, 2009.
Wlaschek, et al., UVA-induced autocrine stimulation of fibroblast-derived collagenase/MMP-1 . . . , Photochem Photobiol. May 1994;59(5):550-6.
Wang, et ano., UVB-irradiated human keratinocytes and interleukin-1alpha . . . , Chin Med J (Engl). May 20, 2006;119(10):827-31.
Fisher, PhD et al., MDMechanisms of Photoaging and Chronological Skin Aging. Arch. Dermatol., vol. 138, 1462-1470, 2002.

* cited by examiner

*Primary Examiner* — Prema Mertz
(74) *Attorney, Agent, or Firm* — Notaro, Michalos & Zaccaria P.C.

(57) ABSTRACT

The present invention relates to cosmetic and dermatological methods for treating cellulite, reducing signs of aging skin, and treating stretch marks, the methods comprising applying/administering to the skin of a subject in need thereof the compositions comprising interleukin-1 alpha.

1 Claim, 1 Drawing Sheet

SEQUENCE LISTING

```
<160> NUMBER OF SEQ ID NOS: 1

<210> SEQ ID NO 1
<211> LENGTH: 159
<212> TYPE: PRT
<213> ORGANISM: Artificial Sequence
<220> FEATURE:
<223> OTHER INFORMATION: Synthetic Peptide

<400> SEQUENCE: 1

Ser Ala Pro Phe Ser Phe Leu Ser Asn Val Lys Tyr Asn Phe Met Arg
1               5                   10                  15

Ile Ile Lys Tyr Glu Phe Ile Leu Asn Asp Ala Leu Asn Gln Ser Ile
            20                  25                  30

Ile Arg Ala Asn Asp Gln Tyr Leu Thr Ala Ala Ala Leu His Asn Leu
        35                  40                  45

Asp Glu Ala Val Lys Phe Asp Met Gly Ala Tyr Lys Ser Ser Lys Asp
    50                  55                  60

Asp Ala Lys Ile Thr Val Ile Leu Arg Ile Ser Lys Thr Gln Leu Tyr
65                  70                  75                  80

Val Thr Ala Gln Asp Glu Asp Gln Pro Val Leu Leu Lys Glu Met Pro
                85                  90                  95

Glu Ile Pro Lys Thr Ile Thr Gly Ser Glu Thr Asn Leu Leu Phe Phe
            100                 105                 110

Trp Glu Thr His Gly Thr Lys Asn Tyr Phe Thr Ser Val Ala His Pro
        115                 120                 125
```

-continued

```
Asn Leu Phe Ile Ala Thr Lys Gln Asp Tyr Trp Val Cys Leu Ala Gly
    130             135             140

Gly Pro Pro Ser Ile Thr Asp Phe Gln Ile Leu Glu Asn Gln Ala
145             150             155
```

METHOD OF REDUCING AGING OF SKIN BY APPLYING INTERLEUKIN-1 ALPHA

CROSS REFERENCE TO RELATED APPLICATION

This is a continuation-in-part application of international patent application PCT/EP2008/054574, filed Apr. 16, 2008, that designates the United States of America, and which is incorporated here by reference.

FIELD OF THE INVENTION

The present invention relates to cosmetic and dermatological methods for improving skin health and appearance. In particular, it relates to cosmetic and/or dermatological methods comprising applying/administering to the skin compositions comprising interleukin-1 alpha.

BACKGROUND OF THE INVENTION

Dermis is a skin layer between epidermis and hypodermis, the layer containing fibroblasts that are involved in producing components of dermis. Up to 85% of dermis consists of collage. A variety of intrinsic and extrinsic factors may affect production of components of dermis and especially collagen, thus, leading to undesirable outward visible and tactilely perceptible changes in skin. For example, chronological aging is accompanied with loss of components of dermis and development of discontinuities in dermis structure that contributes to wrinkles and lines formation, loss of skin elasticity and firmness. Another factor is a mechanical tension of skin of subjects that is frequently observed, e.g. under pregnancy, during growth spurts, and gain weight. This tension factor may lead to development of tears in the dermis known as stretch marks. Excessive regional fat under cellulite may induce weakening dermis structure, fat protrusions into lower dermis, and uneven distribution of subcutaneous tissue giving rise to outward visibly and tactilely perceptible an irregular, dimpled skin surface also known as "orange peel". Thus, there is a great need in safe and effective agents for the improvement of dermis components production reducing dermis discontinuities under abovementioned unfavorable conditions.

Interleukin-1 alpha, which is also named IL-1F1, is a naturally occurring polypeptide with the sequence well-known from the art. Interleukin-1 alpha is synthesized as 31-kDa precursor, and is secreted by cells in active form of about 18-kDa. Interleukin-1 alpha is the only interleukin-1 family member that is constitutively produced in active form by human epidermis in norm. Healthy human skin contains interleukin-1 alpha in levels of about 10 to 13 ng/g, which levels are frequently decreased, for example, in conditions of psoriatic or aging skin. Mizutani H, et al., *J Clin Invest.* 1991, 87(3):1066-71. Wood L C, et al., *J Clin Invest* 1992: 90: 482-487. Se Kyoo Jeong, et al., *Exp. Dermatology* 2005: 14: 571-579. Chantel O., et al., *J Invest Dermatol* 122:330-336, 2004. Nowinski D, et al, *J Invest Dermatol.* 2002; 119(2): 449-55. Bonifati C, et al., *J Biol Regul Homeost Agents.* 1997, 11(4):133-6. Takematsu H, et al. *Tohoku J Exp Med.* 1990, 161(3):159-69.

The use of interleukin-1 alpha in medicinal applications is known from the art. For example, U.S. Pat. No. 4,816,436 discloses a process for treating arthritis or inflammation with the use of intra-articular, intramuscular, intravenous, or intraperitoneal injections of interleukin-1 alpha; U.S. Pat. No. 5,120,534 discloses a method for treating thrombocytopenia by administering interleukin-1 alpha or Asp36, Ser141-derivative of interleukin-1 alpha; U.S. Pat. No. 5,534,251 discloses stabilized medicinal composition comprising Asp36, Ser141-derivative of interleukin-1 alpha; EP0391444 discloses a pharmaceutical composition comprising interleukin-1 alpha, and suitable for forming a parenterally administratable aqueous formulation; WO9116916, JP4018033, EP0482213, and ES2121782T disclose an antitumor composition containing the combination of interleukin-1 and gamma-interferon.

Although interleukin-1 alpha stimulates dermal production of procollagen, the collagen precursor, by dermal fibroblasts, it also stimulates production of collagenase, the collagen destroying enzyme. Postlethwaite et al., *J Cell Biol.* 1988, 106(2):311-8. Duncan et al., *J Invest Dermatol.* 1989, 92(5):699-706. Thus, it is not known from the art, whether applying interleukin-1 alpha to the skin produces overall positive or negative effect on collagen content in skin and dermis density. No published or disclosed in the art related to cosmetic and dermatological methods for treating cellulite, stretch marks, or reducing signs of aging skin with topically applied interleukin-1 alpha.

SUMMARY OF THE INVENTION

Surprisingly, we found that interleukin-1 alpha is useful as an active ingredient in cosmetic or dermatological compositions for keeping a skin in a good condition, reducing signs of aging skin, treating cellulite and/or stretch marks.

It is an object of the present invention to provide cosmetic or dermatological methods for treating cellulite, reducing signs of aged skin, and/or treating stretch marks, the methods comprising applying to the skin compositions comprising interleukin-1 alpha.

DETAILED DESCRIPTION OF THE INVENTION

Figure 1A:
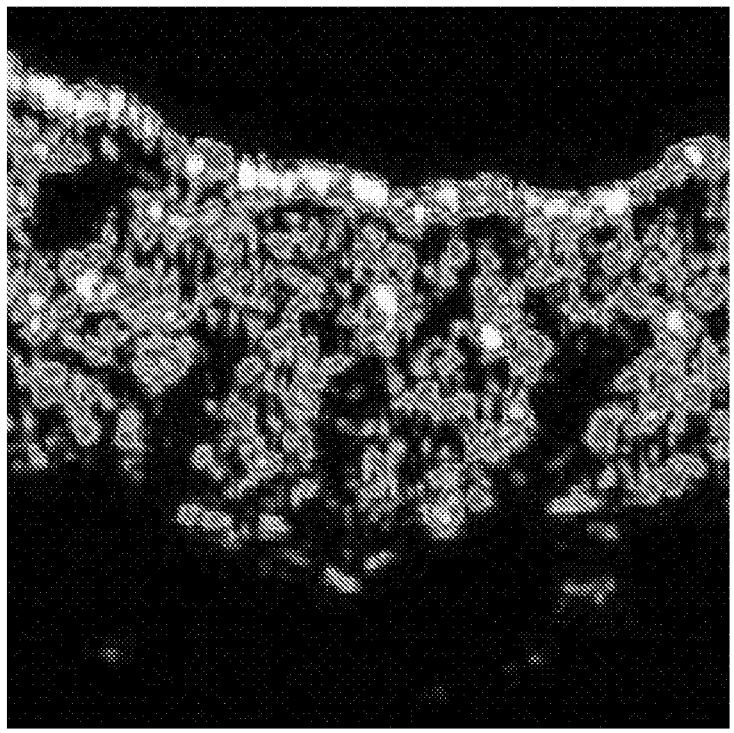
FIGS. 1A and 1B are ultrasonograms showing the improvement of collagen network in dermis in the cellulite affected region of skin two weeks after the topical applying the composition comprising interleukin-1 alpha (FIG. 1B) as compared to that just before the treatment (FIG. 1A). Bright pixels show epidermis echo and fibrous network consisting of collagen and elastin in dermis. Dark pixels show fat depositions in dermis and fat protrusions into lower dermis.

The present invention provides a cosmetic or dermatological method for treating cellulite, the method comprising a step of applying to the skin of a subject in need thereof a composition comprising interleukin-1 alpha and a dermatologically acceptable carrier As used herein, the term "interleukin-1 alpha" refers to a protein having the following amino acid sequence and structure (naturally occurring human interleukin-1 alpha), and biologically active analogues and derivatives thereof:

Ser-Ala-Pro-Phe-Ser-Phe-Leu-Ser-Asn-Val-Lys-Tyr-

Asn-Phe-Met-Arg-Ile-Ile-Lys-Tyr-Glu-Phe-Ile-Leu-

Asn-Asp-Ala-Leu-Asn-Gln-Ser-Ile-Ile-Arg-Ala-Asn-

Asp-Gln-Tyr-Leu-Thr-Ala-Ala-Ala-Leu-His-Asn-Leu-

Asp-Glu-Ala-Val-Lys-Phe-Asp-Met-Gly-Ala-Tyr-Lys-

-continued

Ser-Ser-Lys-Asp-Asp-Ala-Lys-Ile-Thr-Val-Ile-Leu-
Arg-Ile-Ser-Lys-Thr-Gln-Leu-Tyr-Val-Thr-Ala-Gln-
Asp-Glu-Asp-Gln-Pro-Val-Leu-Leu-Lys-Glu-Met-Pro-
Glu-Ile-Pro-Lys-Thr-Ile-Thr-Gly-Ser-Glu-Thr-Asn-
Leu-Leu-Phe-Phe-Trp-Glu-Thr-His-Gly-Thr-Lys-Asn-
Tyr-Phe-Thr-Ser-Val-Ala-His-Pro-Asn-Leu-Phe-Ile-
Ala-Thr-Lys-Gln-Asp-Tyr-Trp-Val-Cys-Leu-Ala-Gly-
Gly-Pro-Pro-Ser-Ile-Thr-Asp-Phe-Gln-Ile-Leu-Glu-
Asn-Gln-Ala (SEQ ID NO: 1).

The term thus includes interleukin-1 alpha which is chemically synthesized or expressed using recombinant protein expression systems that use, for example, *E-coli* or yeast as the host. A preferred interleukin-1 alpha is human interleukin-1 alpha expressed using a protein expression system.

As used herein, the term "analogue of interleukin-1 alpha" refers to an interleukin-1 alpha that contains one or more amino acid substitutions, deletions, additions, or rearrangements compared with human interleukin-1 alpha at sites such that the interleukin-1 alpha analogue still retains the in vivo biological activity of interleukin-1 alpha. Examples of interleukin-1 alpha analogues include Asp36-interleukin-1 alpha and Ser141-interleukin-1 alpha.

Interleukin-1 alpha derivatives include naturally occurring interleukin-1 alpha and interleukin-1 alpha analogues that are chemically or enzymatically derivatized at one or more constituent amino acids, including side chain modifications, backbone modifications, and N- and C-terminal modifications, by for example acetylation, acylation, hydroxylation, methylation, amidation, phosphorylation, pegylation, or glycosylation, and that retain the in vivo biological activity of interleukin-1 alpha. An example of an interleukin-1 alpha derivative is N6-myristoyl-Lys11-interleukin-1 alpha and HisTag-interleukin-1 alpha.

In preferred embodiments of the present invention, the content of interleukin-1 alpha in said compositions is in the range from $10^{-7}$ to $10^{-2}$ wt. %.

In preferred embodiments of the present invention, said compositions further comprise a buffer at a concentration effective to maintain the pH of the composition at between about 4.0 to about 7.5. Examples of dermatologically or cosmetically acceptable buffers include, but are not limited to, phosphate buffer, acetate, citrate buffer, succinate buffer, and glycine buffer.

As used herein, the term "skin" encompasses whole skin or any portion of the skin. In practicing the method for treating cellulite, the preferred portions of skin are thigh, hips, buttocks, and abdomen regions.

As used herein, the term "dermatologically acceptable carrier" refers to one or more liquid, semi-solid, or solid diluents, which are compatible with interleukin-1 alpha, and are suitable for administration to any portion of the human skin suitable without undue/unacceptable effects. Examples of such carriers include, but are not limited to, distilled or deionized water, propyleneglycol, glycerol, and oil.

As used herein, the term "cellulite" refers to gynoid lipodystrophy that is characterized by the uneven distribution of subcutaneous adipose tissue giving rise to an irregular, dimpled skin surface also named "orange peel", especially in the regions of the thighs, abdomen, and/or buttocks. In practicing the method of the present invention, the compositions of the present invention are especially useful for regulating the production of collagen and elastin in dermis of cellulite-affected regions of skin, reducing dermis discontinuities, lowering fat depositions in dermis, and fat protrusions into lower dermis. Because of improving collagen/elastin production in dermis of the cellulite-affected regions with the methods of the present invention, it is now possible to delay, minimize, prevent, ameliorate, and/or diminish cellulite severity, visible and/or tactile discontinuities in skin, especially in the skin surface.

Further, the present invention provides a cosmetic or dermatological method for reducing a sign of aging skin, the method comprising a step of applying to the skin a composition comprising interleukin-1 alpha and a dermatologically acceptable carrier.

In preferred embodiments of the present invention, the content of interleukin-1 alpha in said compositions is in the range from $10^{-7}$ to $10^{-2}$ wt. %.

In preferred embodiments of the present invention, said compositions further comprise a buffer at a concentration effective to maintain the pH of the composition at between about 4.0 to about 7.5. Examples of dermatologically or cosmetically acceptable buffers include, but are not limited to, phosphate buffer, acetate, citrate buffer, succinate buffer, and glycine buffer.

In practicing the method of the present invention, the compositions of the present invention are useful for regulating the skin condition (skin conditioning), visible and/or tactile discontinuities caused by irregularities of skin dermis. Such discontinuities may be induced or caused by internal and/or external factors, and include the signs of skin aging described herein. The term "regulating skin condition" includes delaying, minimizing and/or preventing, ameliorating, e.g., diminishing, minimizing and/or effacing visible and/or tactile discontinuities in skin. Regulating skin condition involves improving skin appearance and/or feel.

In practicing the method of the present invention, the compositions of the present invention are particularly advantageous for regulating signs of skin aging, more especially visible and/or tactile discontinuities in skin texture associated with aging. "Regulating the signs of skin aging" includes regulating one or more of such signs (similarly, regulating a given sign of skin aging, e.g., lines, wrinkles or pores). As used herein, regulating such signs includes delaying, minimizing, preventing, ameliorating, e.g., diminishing, minimizing and/or effacing signs of skin aging.

"Signs of skin aging" include, but are not limited to, all outward visibly and tactilely perceptible manifestations of dermis discontinuities as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles, including both fine superficial wrinkles and coarse deep wrinkles, skin lines, crevices, bumps, large pores, scaliness, flakiness and/or other forms of skin unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the, dermis, and tissues proximate to the dermis.

In practicing the present invention, the compositions of the present invention are particularly advantageous for improving skin elasticity and firmness.

In practicing the present invention, the compositions of the present invention are particularly advantageous for enhancing production of components of dermis, e.g. collagen, elastin, and hyaluronic acid.

Further, the present invention provides a method for treating a stretch mark, the method comprising a step of administering to the skin of a subject in need thereof a composition comprising interleukin-1 alpha and a dermatologically acceptable carrier.

As used herein, the term "stretch mark" refers to a tear in the dermis also called striae and accompanied with losing collagen and elastin. Because of improving collagen/elastin production in dermis of the stretch mark-affected regions with the methods of the present invention, it is now possible to delay, minimize, prevent, ameliorate, and/or diminish stretch marks severity in a subject in need thereof. Such subjects include, but are not limited to, women after pregnancy, teenagers during growth spurts, individuals that gain weight, body builders, and individuals after steroid therapy.

In preferred embodiments of the present invention, the content of interleukin-1 alpha in said compositions is in the range from $10^{-7}$ to $10^{-2}$ wt. %.

In preferred embodiments of the present invention, said compositions further comprise a buffer at a concentration effective to maintain the pH of the composition at between about 4.0 to about 7.5. Examples of dermatologically or cosmetically acceptable buffers include, but are not limited to, phosphate buffer, acetate, citrate buffer, succinate buffer, and glycine buffer.

In practicing the cosmetic methods of the present invention, the compositions may be administered by topical applying to the skin of a subject in need thereof one or two times per day for one day or more, preferably, from seven days to two months.

In practicing the dermatological methods of the present invention, the compositions may be administered by a variety of routes. Such routes include, but are not limited to, topical, intradermal, or mesodermal.

As used herein, the term "dermatologically acceptable carrier" refers to one or more liquid, semi-solid, or solid diluents, which are suitable for administration to any portion of the human skin, and are compatible with the interleukin-1 alpha and other active or optional ingredients of the present invention. Examples of such carriers include, but are not limited to, distilled or deionized water, propyleneglycol, glycerol, and oil.

The compositions of the present invention can comprise optional ingredients. Such optional ingredients generally are used individually at levels from about 0.0005% to about 10.0%, preferably from about 0.005% to about 1.0% by weight of the composition.

Examples of suitable optional ingredients include, but are not limited to, depigmentation agents; reflectants; humectants; antimicrobial (e.g., antibacterial) agents; UV absorbers; anti-acne agents; anti-aging agents; anti-wrinkling agents, antiseptics; local anesthetics; wound healing promoters; deodorants and antiperspirants; skin emollients and skin moisturizers; tanning agents; skin lightening agents; antifungals; depilating agents; external analgesics; counterirritants; anti-diaper rash agents; make-up preparations; vitamins and nutrients such as thiamin, riboflavin, niacin, pantothenates, pyridoxine, folic acid, cobalamin, biotin, choline, inositol, ascorbic acid, lipoic acid, carnitine, and etc.; amino acids and their derivatives such as alanine, arginine, asparagine, aspartic acid, carnitine, citrulline, cysteine, dimethylglycine, gamma-aminobutyric acid, glutamic acid, glutamine, glutathione, glycine, histidine, isoleucine, leucine, lysine, methionine, ornithine, phenylalanine, praline, serine, taurine, threonine, tryptophan, tyrosine, valine; minerals such as boron, calcium, chromium, cobalt, copper, fluoride, germanium, iodine, iron, lithium, magnesium, manganese, molybdenum, phosphorus, potassium, selenium, silicon, sodium, sulfur, vanadium, zinc; herbal extracts; retinoids; bioflavonoids; anti-oxidants; skin conditioners; hair lighteners; chelating agents; cell turnover enhancers; coloring agents; sunscreens and the like; alpha- and beta-hydroxyacids; agents for chemical peeling; and mixtures thereof.

Examples of suitable reflectants include, but not limited to, mica, alumina, calcium silicate, glycol dioleate, glycol distearate, silica, sodium magnesium fluorosilicate, and mixtures thereof.

Examples of suitable UV absorbers include, but not limited to, benzophenone, bomelone, butyl paba, cinnamidopropyl trimethyl ammonium chloride, disodium distyrylbiphenyl disulfonate, paba, potassium methoxycinnamate, and mixtures thereof.

Examples of suitable humectants include, but not limited to, water soluble liquid polyols selected from the group comprising glycerine, propylene glycol, hexylene glycol, butylene glycol, pentylene glycol, dipropylene glycol, and mixtures thereof. The humectant is preferably present in an amount of from about 0 percent to about percent, more preferably from about 0.5 percent to about 5 percent, based on the overall weight of the composition.

Suitable amino acid agents include amino acids derived from the hydrolysis of various proteins as well as the salts, esters, and acyl derivatives thereof. Examples of such amino acid agents nonexclusively include amphoteric amino acids such as alkylamido alkylamines, i.e. stearyl acetyl glutamate, capryloyl silk amino acid, caprylol collagen amino acids; capryloyl kertain amino acids; capryloyl pea amino acids; cocodimonium hydroxypropyl silk amino acids; corn gluten amino acids; cysteine; glutamic acid; glycine; hair keratin amino acids; hair amino acids such as aspartic acid, threonine, serine, glutamic acid, glycine, alanine, half-cystine, valine, methionine, isoleucine, leucine, tyrosine, phenylalanine, cysteic acid, lysine, histidine, arginine, cysteine, tryptophan, citrulline; lysine; silk amino acids, wheat amino acids; and mixtures thereof Examples of suitable proteins include, but not limited to, collagen, deoxyribonuclease, iodized corn protein; keratin; milk protein; protease; serum protein; silk; sweet almond protein; wheat germ protein; wheat protein; wheat protein, alpha and beta helix of keratin proteins; hair proteins, such as intermediate filament proteins, high-sulfur proteins, ultra-high-sulfur proteins, intermediate filament-associated proteins, high-tyrosine proteins, high-glycine tyrosine proteins, tricohyalin, arginine-rich peptides like as oligoarginines $(Arg)_8$, and mixtures thereof.

Examples of suitable antiperspirants and deodorants include, but not limited to, aluminium chlorohydrates, aluminium zirconium chlorohydrates, and mixtures thereof.

Examples of sunscreen agents include, but not limited to, titanium dioxide and zinc oxide.

Examples of suitable counterirritants include, but not limited to, camphor, menthol, methyl salicylate, peppermint and clove oils, ichtammol, and mixtures thereof.

Examples of suitable anti-aging agents include, but are not limited to, inorganic sunscreens such as zinc oxide; organic sunscreens such as octyl-methyl cinnamates and derivatives thereof; retinoids; vitamins such as vitamin C, vitamin B, and derivatives thereof; antioxidants including acid such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrrolactic acid, alpha-hydroxyisovaleric acid, ethyl pyruvate, galacturonic acid, glucopehtonic acid, glucopheptono 1,4-lactone, gluconic acid, gluconolactone, glucuronic acid, glucurronolactone, glycolic acid, isopropyl pyruvate, methyl pyruvate, mucic acid, pyruvia acid, saccharic acid, saccaric acid 1,4-lactone, tartaric acid, and tartronic acid; succinic acid or salts thereof; acids such as beta-hydroxybutyric acid, beta-phenyl-lactic acid, beta-phenylpyruvic acid; botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, rice, safflower, and mixtures thereof. Suitable amounts of anti-aging agents include, based upon the total weight of the composition, from about 0.01 percent to about 10 percent, and preferably from about 0.04 percent to about 5 percent.

Examples of suitable depigmentation agents include, but are not limited to, hydroquinone and it derivatives; vitamins such as niacin, vitamin C and its derivatives; extracts such as chamomile and green tea, and mixtures thereof.

Examples of skin lightening agents include, but not limited to, hydroquinone, catechol and its derivatives, ascorbic acid and its derivatives, and mixtures thereof.

The compositions of the invention are prepared by well-known procedures. Such procedures include, but are not limited to, mixing the interleukin-1 alpha with other ingredients of the composition in conventional manner. Guidance for the preparation of cosmetic or dermatological compositions of the invention can be found in "Remington: The science and practice of pharmacy" 20th ed. Mack Publishing, Easton Pa., 2000 ISBN 0-912734-04-3 and "Encyclopaedia of Pharmaceutical Technology", edited by Swarbrick, J. & J. C. Boylan, Marcel Dekker, Inc., New York, 1988 ISBN 0-8247-2800-9 or a newer edition. As well known to the skilled person, illustrative additives to dermatological compositions include, but is not limited to: ointment bases, solvents, buffering agents, pH-adjusting agents, preservatives, humectants, chelating agents, antioxidants, stabilizers, emulsifying agents, suspending agents, gel-forming agents, perfumes, and skin protective agents.

The compositions of the present invention can be formulated in a variety of forms including, but are not limited to, lotions, gels, creams, sprays, and solutions. The compositions of the invention are prepared by methods well-known from the art in accordance with accepted procedures in a variety of forms. Such forms include, but are not limited to, solution, lotion, gel, emulsion, spray, and cream.

In practicing the methods of the present invention, an effective amount of the composition of the invention is applied/administered to the skin of a subject in need thereof, and is preferably left on the skin for a period of at least about 15 minutes, more preferably at least about 30 minutes, even more preferably at least about 1 hour, most preferably for at least several hours, e.g., up to about 12 hours. This method can be reapplied from 1 to about 5, preferably from 1 to 3 times per day. Typically, the effective amount of the composition is from about 1 gram to about 100 grams, preferably from about 1 gram to about 20 grams.

The following examples are presented to demonstrate the invention. The examples are illustrative only and are not intended to limit the scope of the invention in any way.

Example 1

This example demonstrates the composition of the invention.

| Ingredient | Content, wt. % |
|---|---|
| hr-Interleukin 1 alpha | 0.00001 |
| Phosphate buffer | qs to pH 5.5 |
| Distilled water | to 100 |

The solution preparation: human recombinant interleukin-1 alpha is mixed with other ingredients in the conventional manner to prepare the composition.

The cosmetic or dermatological method for treating skin: 1 ml of the composition is topically applied to the facial skin, and is preferably left on the skin for a period of at least about 15 minutes.

Example 2

This example demonstrates the cosmetic method for the treatment of cellulite.

The composition comprising 0.00001 wt. % of interleukin-1 alpha was applied twice-a-day for eight weeks to the cellulite-affected skin region of thighs of fifteen women aged≧35 years with body fat index (BFI)≧25 (33.9×0.9).

Cellulite is significantly related to irregularity of dermis and dermis-hypodermis junction surface caused by fat deposition in dermis and fat protrusions to the lower dermis, the irregularities giving rise to visible irregularity of skin surface. Smalls L K et al., Quantitative model of cellulite: three-dimensional skin surface toporaphy, biophysical characterization, and relationship to human perception. *J Cosmet Sci.* 2005, 56(2):105-20. The efficacy of the composition for the reducing cellulite severity was assessed by ultrasonography, using a Dermascan® device at 20-Mhz frequency; and by measurement of thigh girths. Results obtained at eight week of the treatment are presented in the Table below in percent of changes of mean to basal level (just before the treatment).

| Measure | Average change |
|---|---|
| Dermis-hypodermis junction distance | −23% |
| Number of dark pixels (fat depositions in dermis) | −27% |
| Number of bright pixels (collagen plus elastin in dermis) | +27% |
| Thigh Girth | −0.5 cm |

Figure 1B:
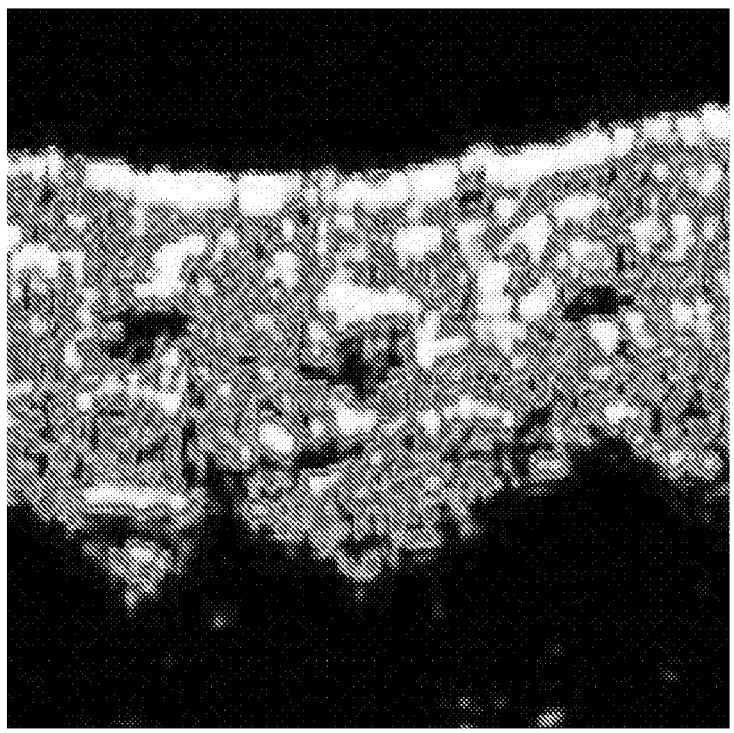

Thus, the example shows that topical applying the composition comprising interleukin-1 alpha is effective for treating cellulite, especially for reducing dermis-hypodermis junction distance that is accompanied with diminishing the irregularity of skin surface ("orange peel") in the cellulite-affected skin regions. The representative ultrasonogram of the skin in cellulite-affected region just before the treatment and after the treatment with the composition of the present invention is presented in FIG. 1.

Example 3

This example demonstrates the cosmetic method for reducing signs of aging skin, improving skin elasticity and firmness, and skin conditioning.

The 1 ml of the composition comprising 0.00001 wt. % of interleukin-1 alpha was applied twice-a-day for eight weeks to the aging sign-affected skin regions of faces of ten women aged≧45 years. The efficacy of the composition for the reducing signs of aging skin was assessed by a battery of tests. Skin substructure (epidermis plus dermis thickness, dermis density, and collagen) was assessed by ultrasonography, using Dermascan® device with 20-Mhz frequency. Micro-wrinkles deepness and orientation were assessed by profilometry. Deep wrinkles were assessed by laser profilometry on silicon prints. The efficacy of the composition for improving skin elasticity and firmness was assessed by a suction method, using a Cutometer®. The efficacy of the composition for keeping a skin in a good condition, or skin conditioning efficacy, was assessed by transepidermal water loss (TEWL), using a Tewameter®. Results obtained at eight week of the treatment are presented in the Table below in percent of changes of mean to basal level (just before the treatment).

| Measure | Average change |
| --- | --- |
| Epidermis plus dermis thickness | +21% |
| Dermis density | +36% |
| Number of bright pixels (collagen plus elastin in dermis) | +22% |
| Elasticity | +18% |
| Firmness | +29% |
| TEWL | −21% |
| Micro-wrinkles: | |
| Isotropy | +12% |
| Mean depth of furrows | −24% |
| Deep wrinkles: | |
| Mean wrinkle depth | −22% |
| Wrinkle volume | −19% |

Example 4

This example demonstrates the cosmetic method for treating stretch marks. The composition comprising 0.00002 wt. % of interleukin-1 alpha was applied twice-a-day for eight weeks to the stretch mark-affected skin region of low abdomen of three women. At eight week of the treatment, significant decrease stretch marks size and visual appearance was found as compared to basal levels. Also, the dermis density at stretch marks-affected regions was increased.

Example 5

This example demonstrates the dermatological method for treating stretch marks.

The composition comprising 0.000001 wt. % of interleukin-1 alpha was administered mesodermally into the stretch mark-affected region of the skin of three women once-a-day for three consecutive days. Four weeks later, the significant decrease in visual appearance of stretch marks was found. Also, the dermis density at stretch marks-affected regions was increased.

The invention claimed is:

1. A method for reducing a sign of aging skin in a subject in need thereof, the method comprising a step of applying to the skin, a composition comprising an effective amount of interleukin-1 alpha and a dermatologically acceptable carrier, wherein applying the composition to the skin has an effect selected from the group consisting of: reducing the depth and volume of skin wrinkles; improving skin elasticity; improving skin firmness; improving epidermis plus dermis thickness; improving dermis density; improving dermis collagen; and reducing transepidermal water loss, wherein the content of interleukin-1 alpha in said composition is in the range from $10^{-7}$ to $10^{-2}$ wt. %, and wherein the composition further comprises a buffer at a concentration effective to maintain the pH of the composition at between about 4.0 to about 7.5.

* * * * *